United States Patent [19]
Lo

[11] Patent Number: 5,886,903
[45] Date of Patent: Mar. 23, 1999

[54] METHOD AND KNOWLEDGE-BASED SYSTEM FOR DIAGNOSIS IN BIOLOGICAL TREATMENT OF WASTE WATER

[75] Inventor: Amy Chiu-Mei Lo, Baie d'Urfeé, Canada

[73] Assignee: Domtar Inc., Canada

[21] Appl. No.: 729,047

[22] Filed: Oct. 10, 1996

[51] Int. Cl.⁶ .................................................. G06F 19/00
[52] U.S. Cl. ........................ 364/496; 210/601; 395/914
[58] Field of Search .................................. 364/496, 497, 364/498, 499, 500, 502, 551.01, 552, 578; 395/902, 906, 914; 210/601, 709, 739, 745, 85

[56] References Cited

U.S. PATENT DOCUMENTS

| | | | |
|---|---|---|---|
| 5,160,439 | 11/1992 | Dobrez et al. | 210/709 |
| 5,242,602 | 9/1993 | Richardson et al. | 364/498 X |
| 5,481,481 | 1/1996 | Frey et al. | 364/551.01 |
| 5,492,632 | 2/1996 | Reber | 210/739 |

*Primary Examiner*—Melanie Kemper
*Attorney, Agent, or Firm*—Anthony J. Casella; Gerald E. Hespos; Ludomir A. Budzyn

[57] ABSTRACT

A method and knowledge-based system for generating a holistic health index for diagnosis and decision support in operational management of biological treatment of waste water with a microbial population; measured parameters of an operating biological treatment employing a microbial population are compared with benchmark values in a data base to generate a comparison value and a holistic health index of the operating microbial population is generated from the comparison values which provide an evaluation of the operational management of the biological treatment. Based on such evaluation the operating parameters of the treatment may be adjusted to maintain the treatment at an optimum level.

13 Claims, 4 Drawing Sheets

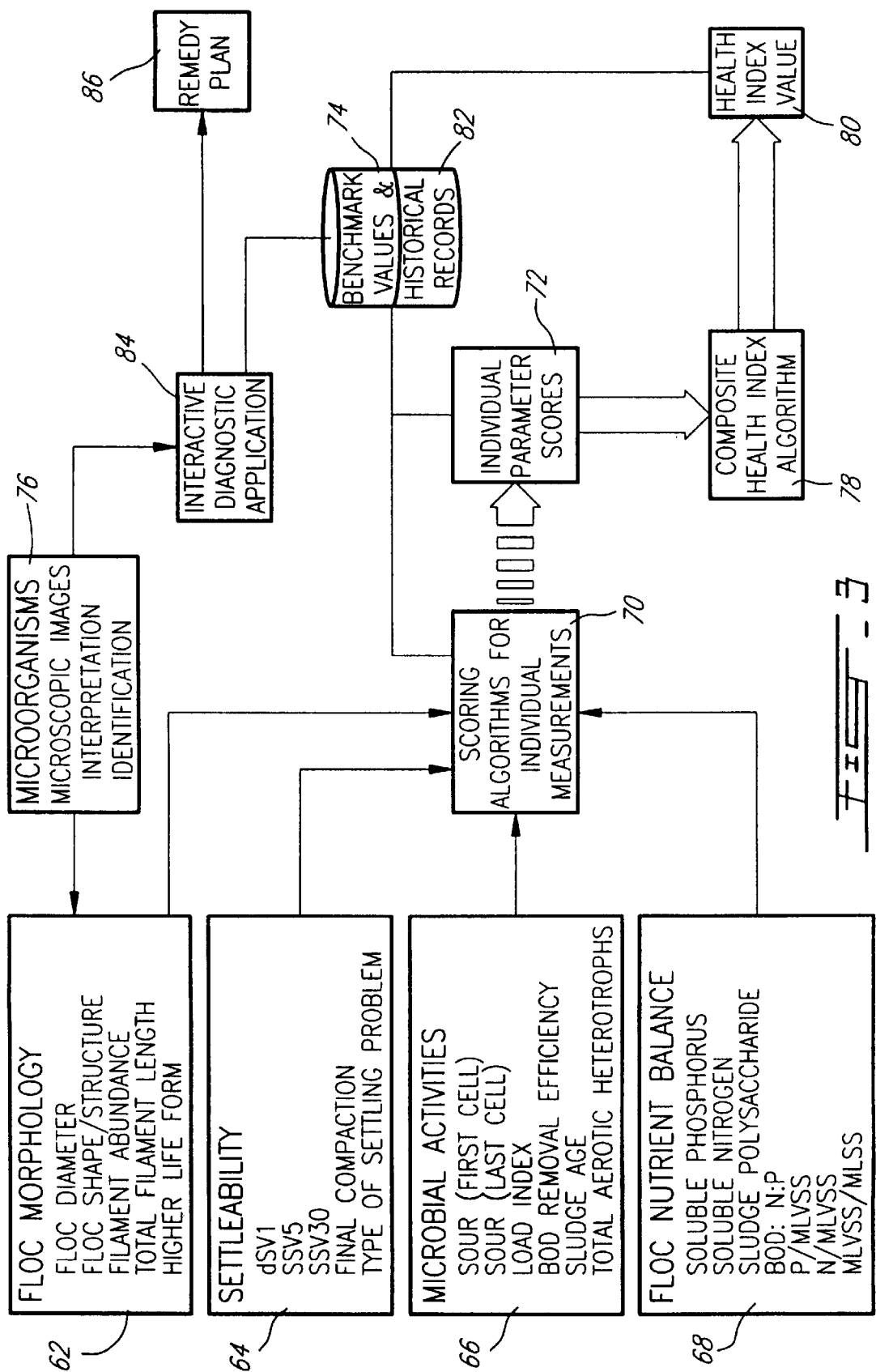

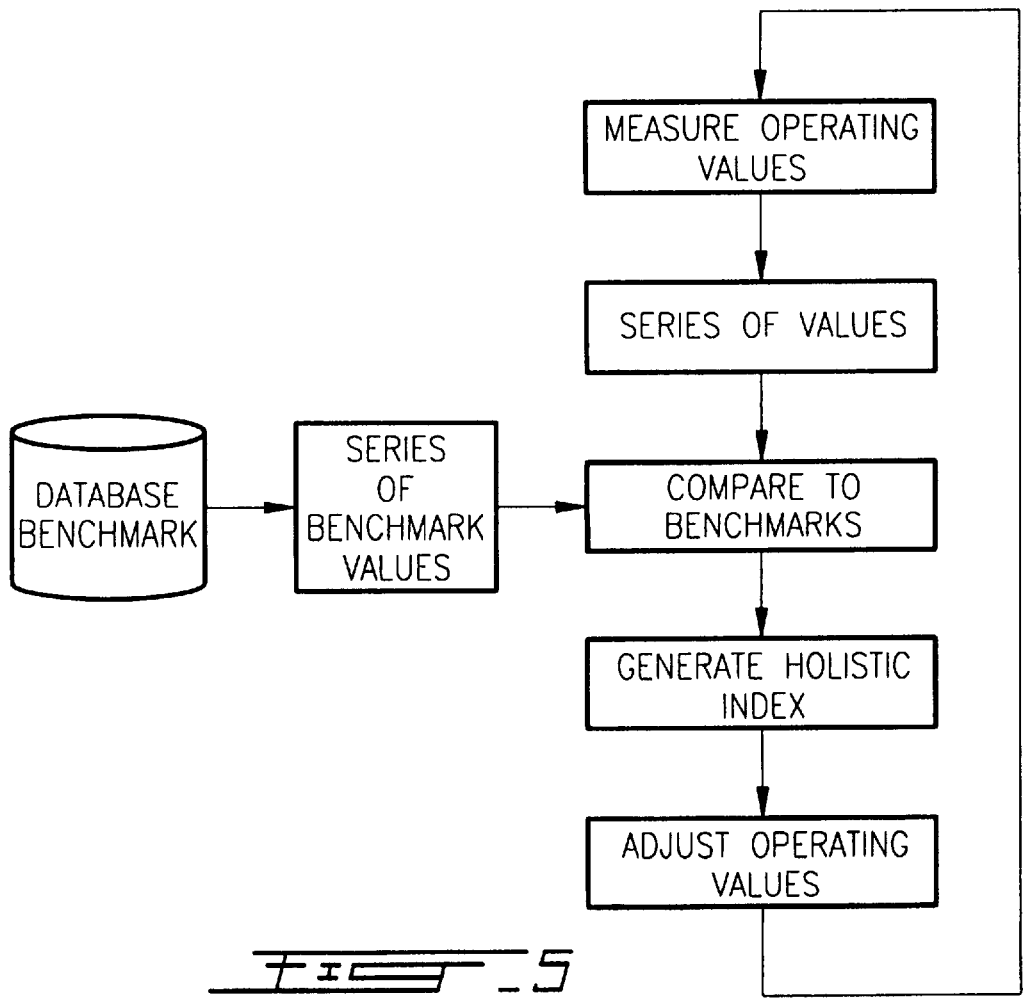

METHOD AND KNOWLEDGE-BASED SYSTEM FOR DIAGNOSIS IN BIOLOGICAL TREATMENT OF WASTE WATER

BACKGROUND OF THE INVENTION a) Field of the Invention

This invention relates to a knowledge-based system for generating a holistic health index for diagnosis and decision support in operational management of biological treatment of waste water with a microbial population; to a method of generating such a holistic health index; and to a method for managing a biological treatment of waste water with a microbial population. The invention has particular application in the treatment of waste water from a pulp and paper mill.

b) Description of Prior Art

Waste water treatment is generally classified as primary or secondary treatment. Primary treatment usually involves a mechanical process to remove sediments and clarifiable solids from the influent and to condition the waste water for secondary treatment. Secondary treatment mainly relies on biological processes to reduce biological oxygen demand (BOD) and certain toxicity in waste water to an acceptable level before it is discharged to the environment. In some industries, effluents from secondary treatment may require further chemical treatment to remove specific toxic materials before discharge.

Microbial activities are the essential component of secondary treatment. The microorganisms function as a biological system with their living environment. The waste water is usually aerated to provide dissolved oxygen to support microbial growth. The microorganisms populate and consume the organic wastes in the waste water. The biological treatment process produces biomass or sludge that has to be removed from the treatment tank. The sludge may promote or hinder the desirable microbial activities depending on its amount in the treatment tank. Treatment is optimal if a delicate balance of sludge is maintained with respect to the input conditions of the influent and other operating parameters.

Because the treatment is biological in nature, influent and other operational conditions directly affect the microbial activities and subsequently the performance of the treatment process. If the microbial living environment favours the desirable microbial activities, good performance is achieved, and vice versa. In extreme cases, the entire microbial population may die as a result of shock or toxicity. Shock may come from excessive input conditions in the influent and from the changing open environment. Toxicity may be present in the influent or it could be self-induced by some microbial activities in certain situations. The microbial population can also be overpopulated by unwanted microorganisms that deteriorate treatment. Recovery time is usually long once the desirable microbial population is gone.

In the case of waste water from a pulp and paper mill compliance with strict environmental regulations may require the mill to shut down its production or reduce its production capacity during the long recovery period when the biological treatment is not proceeding adequately. There is undoubtedly high corporate interest in avoiding costly production loss.

There are at present no easy tools available to field operators to prevent microbial disasters from happening. Prior practice does not provide a comprehensive and holistic measure of the health of the microbial population in the treatment tank as an organic living system in its own right, with respect to its function in the treatment process. Standard field measurements typically focus on monitoring influent and effluent parameters. More sophisticated measurements in areas of floc morphology and identification of specific groups of microorganisms, floc settlability, microbial activity and nutrient balance are all stand-alone approaches. It requires considerable knowledge and experience of a trained person to make an integrated diagnostic comprehension. The field operator can observe operational symptoms when the illness has advanced into an observable operational stage. In many instances it is already too late to avoid any loss in mill production. Field operators generally are not trained to have the knowledge or the specialized skills to conduct a microbial diagnosis of the illness symptoms or to prevent microbial disasters from happening in the first place.

SUMMARY OF THE INVENTION

It is an object of this invention to provide a knowledge-based system for generating a holistic health index for diagnosis and decision support in operational treatment of waste water with a microbial population.

It is another object of this invention to provide a method of generating a holistic health index for diagnosis and decision support in operational management of biological treatment of waste water with a microbial population.

It is yet another object of this invention to provide a method for managing a biological treatment of waste water with a microbial population.

In accordance with one aspect of the invention there is provided a knowledge based system for generating a holistic health index for diagnosis and decision support in operational management of biological treatment of waste water with a microbial population comprising:

a) data base means having a store of benchmark values of a plurality of parameters for biological treatment of waste water with a first microbial population, b) input means for acquiring measured values of second parameters in an operating biological treatment of waste water with a second microbial population, said second parameters corresponding to at least some of said plurality of parameters, c) comparison means for comparing said measured values with corresponding ones of said benchmark values and generating a comparison value for each of the second parameters, d) index generating means for generating a holistic health index of said second microbial population from the comparison values, said health index providing an evaluation of the operational management of the biological treatment with said second microbial population.

In accordance with another aspect of the invention there is provided a method of generating a holistic health index for diagnosis and decision support in operational management of biological treatment of waste water with a microbial population comprising:

i) establishing a data base with stored benchmark values of a plurality of parameters for the biological treatment of waste water, with a first microbial population, ii) measuring operating values of said parameters in a biological treatment of waste water with a second microbial population, iii) comparing the measured operating values from ii) with said benchmark values and generating a comparison value for each of the parameters, and iv) generating a holistic health index of said second microbial population from the comparison values, said health index providing an evaluation of the operation of the biological treatment with said second microbial population.

In accordance with get another aspect of the invention there is provided a method for managing a biological treatment of waste water with a microbial population comprising:

i) establishing a data base with stored benchmark values of a plurality of parameters for the biological treatment of waste water, with a first microbial population, ii) measuring operating values of said parameters in a biological treatment of waste water with a second microbial population, iii) comparing the measured operating values from ii) with said benchmark values and generating a comparison value for each of the parameters, iv) generating a holistic health index of said second microbial population from the comparison values, said health index providing an evaluation of the operation of the biological treatment with said second microbial population, and v) adjusting said operating values in response to the holistic health index to maintain said biological treatment at an optimum level.

BRIEF DESCRIPTION OF DRAWINGS

FIG. 3 illustrates schematically generation of the holistic health index in accordance with the invention; and FIGS. 4 and 5 are flow charts illustrating the invention.

DESCRIPTION OF PREFERRED
EMBODIMENTS WITH REFERENCE TO THE
DRAWINGS

Figure 1:
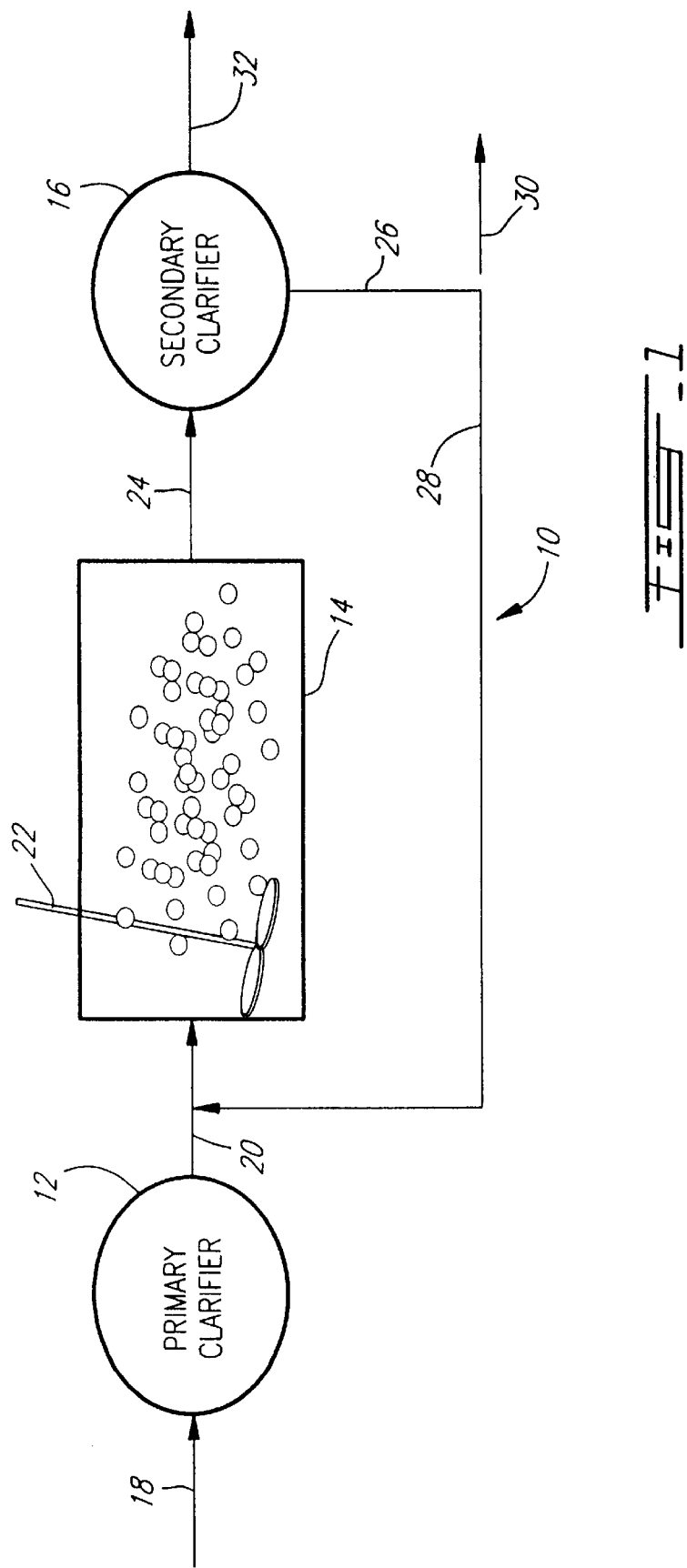
FIG. 1 illustrates schematically a typical waste water treatment to which the invention may be applied.

With further reference to FIG. 1 there is illustrated a typical waste water treatment process installation 10 having a primary clarifier 12, a biological treatment tank 14 and a secondary clarifier 16.

Raw waste water enters primary clarifier 12 by an inlet line 18. Line 20 connects primary clarifier 12 and tank 14; waste water clarified in primary clarifier 12 flows along line 20 as an influent to tank 14. Waste water in tank 14 is aerated with one or more mechanical aerators 22 which entrain air in the water and increase the dissolved oxygen content. Tank 14 houses the microbial population.

The biological treatment of the waste water takes place in tank 14.

Biologically treated water flows from tank 14 along line 24 to secondary clarifier 16 where a further mechanical clarification is conducted. Settled solids from clarifier 16 exit through line 26, a portion of the solids removed in line 26 are fed by recycle line 28 back to line 20 to retain biomass concentration in tank 14 and excess solids are discharged by discharge line 30.

Clarified effluent is discharged from clarifier 16 at line 32. Line 32 usually discharges to the natural environment.

Figure 2:
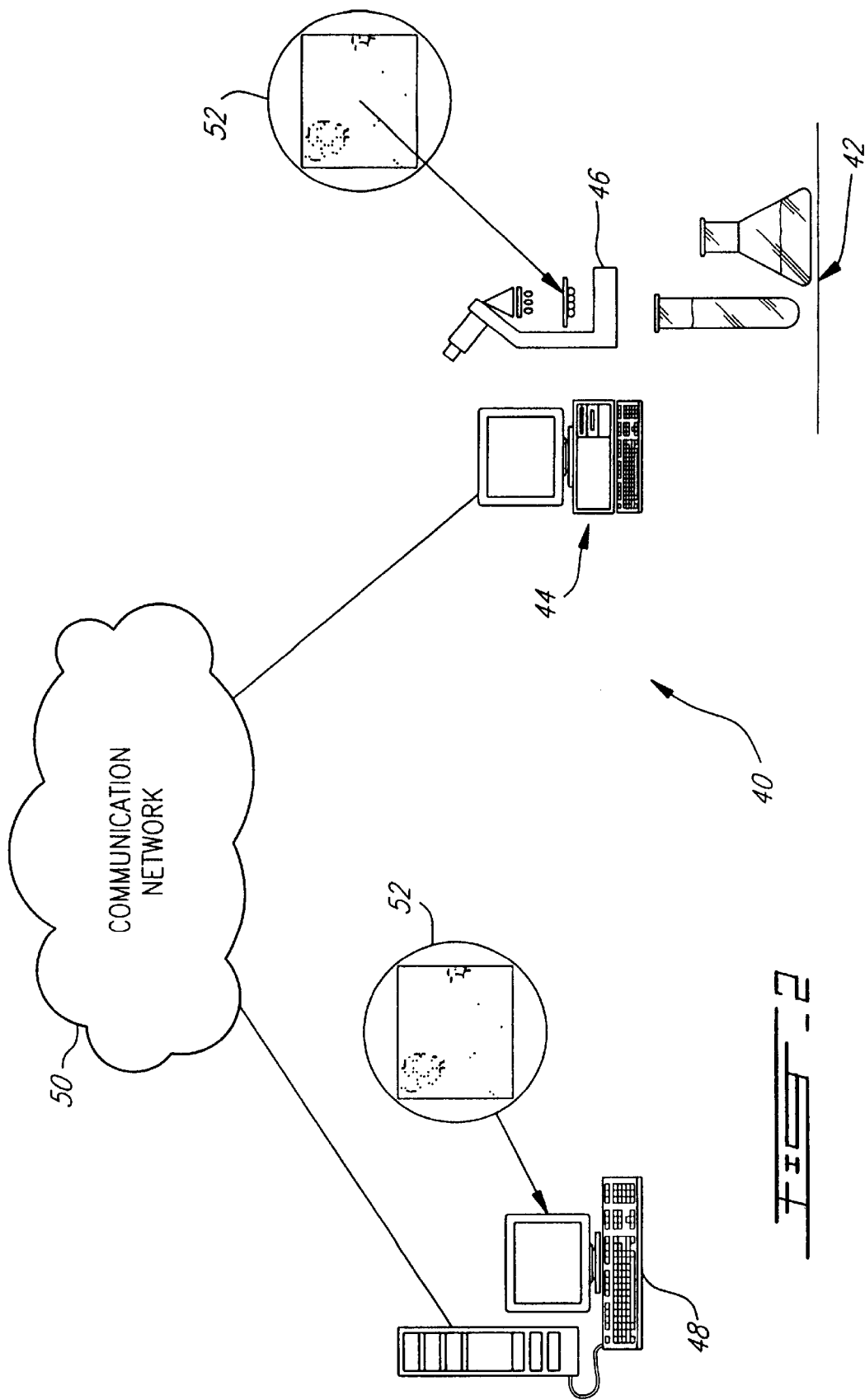
FIG. 2 illustrates schematically a knowledge-based system of the invention.

With further reference to FIG. 2, a knowledge based system 40 includes a stand-alone operations data station 42, a computer data base and application 44 and a live microscopic image station 46. A remote knowledge station 48 is electronically connected through a communication network 50 to computer data base 44.

Physical measurements such as floc settlability, microbial activity and nutrient balance are measured at operational data station 42 and the measurements are entered into computer data base 44.

Live microscopic images 52 are captured at image station 46 and digitally stored in computer data base 44, and may be used to evaluate floc morphology. The images 52 in live or still form may be transmitted by network 50 to remote knowledge station 48 for interactive on-line and off-line interpretation or consultation.

With further reference to FIG. 3, representative physical measurement of parameters to be carried out at station 42 in FIG. 2 include floc settlability 64, microbial activities 66 and nutrient balance 68 which are keyed into data base 44.

The parameters 64, 66 and 68 are scored by scoring algorithms 70 which map the measured parameters of the live operating microbial population to a score 72 for each parameter. Score 72 employs benchmark values 74 for the microbial population which are empirically pre-established.

Live microscopic images 52 are inventoried and digitally stored in data base 44. The images 52 may be communicated to remote knowledge station 48 for examination by a knowledgeable observer, and an input 76 is made to diagnostic application 84 with information as to the type of specific microorganisms. The input 76 developed from images 52 is used to support the measurement of floc morphology 62. The scoring algorithm 70 generates a score 72 for the measurement 62 against benchmark values 74.

The benchmark values 74 are typically derived from operational statistics for the industry as a whole, specific operational considerations provided by the system implementation expert; and continuous learning input from the knowledge user. In particular, they are the values from an optimally performing population of the microorganisms. The proper scoring algorithms 70 used to generate scores 72 for individual measurements against their benchmark values 74 are selected by the knowledge expert at the initial setup stage. All the scoring algorithms 70 are open for adjustment and fine-tuning during the learning phase of the implementation or when the application warrants such a review thereafter.

The final indexing algorithm 78 generates a composite health index 80 for the microbial population in the tank 14 based on the individual scores 72 of all the measurement parameters. The composite health index 80 is tabulated on a linear scale for easy interpretation. The health index 80 directly reflects the desirable types and level of microbial activities in the treatment process with respect to its operational objective. The highest health index 80 value means the treatment process is operating at optimal state according to its design. The lowest health index 80 value means the treatment process is not functioning or totally non-effective to digest the organic wastes. In between, various treatment performance levels, increasing or decreasing risks of having microbial problems and their probable consequences are descriptively mapped onto the index scale for easy interpretation by operational management. The composite health indexing algorithm 78 is open to the knowledge expert for fine-tuning during the learning phase of the implementation.

Health index 80 and scores 72 are kept in a data repository 82 in the computer data base 44 to support auditing of any continuous improvement program. The system 40 also keeps a record of actual treatment performance and incidences.

The operational records provide the continuous learning feedback to validate and improve the mapping of operational reality onto the health index scale.

Based on the composite health index 80 and individual scores 72 of the various input measurements, and interpretation of the input 76 developed from the microbial images 52, a diagnostic application 84 of the system 40 allows the user to identify probable causes for poor microbial activities in the tank 14. System 40 interactively works with the user to identify a remedy plan 86 to restore microbial health and treatment performance.

The function of scoring algorithms 70 is to map a measured parameter value in the live operating system (second microbial population) to a score 72 using the benchmark references 74. Scores are any numeric values on any suitable scaling interval (a, b). In an example case set out in Table I, a=0 and b=3 for all the measured parameters (e.g. 62,64). If the measured parameter value equals the optimal benchmark value 74, the scoring algorithm 70 maps it to a best score of 3 on the scoring scale (a=0, b=3). If the measured value falls at some pre-defined extreme points outside the benchmark range or value 74, the scoring algorithm 70 maps it to a worst score of 0. Between 0 and 3, the scoring algorithms 70 map it to a score in an algorithmic manner depending on the parameters.

Three groups of scoring algorithms 70 are used to assign scores between 0 and 3. Group A scoring algorithms use discrete step functions as the mapping functions between parameter and score. The group A scoring algorithms 70 map ranges of parameter value onto a single integer point. For example, all measured values that coincide with the benchmark 74 have a score 72 of 3. Other measured ranges outside the benchmark 74 are proportionally mapped onto a score 72 of 2, 1 or 0. Physically it means the parameters is considered as having an incremental impact on microbial health only when it has reached certain levels.

Group B scoring algorithms 70 use continuous and linear mapping functions. Every measured parameter value is proportionally mapped onto a point on the continuous score line between a=0 and b=3. If the parameter value has truncated halved-normal, log-normal or any one-sided distribution, then every possible measured value has exactly one score value 72. If the parameter has a two-sided distribution, then a single score 72 may correspond to two possible measured values. Physically it means every parameter value has a proportional impact on microbial health.

Group C scoring algorithms 70 use continuous and non-linear mapping functions, for example, the floc size/morphology parameter. Every measured value is mapped non-linearly onto a point on the continuous score line between a=0 and b=3. Physically it means every parameter value has a non-linear impact on microbial health.

Health indexing algorithm 78 consolidates all the individual parameter scores 72 into an index point on a continuous line scale between 0 and 1. An index 80 of 1 corresponds to the ideal situation of highest scores 72 or optimal measured values in all the parameters. Physically it means the microbial health is at its best and the treatment system is running at optimal condition. An index 80 of 0 means the microbial population responsible for waste water treatment is basically dead.

To assign a composite health index 80, the indexing algorithm 78 first relatively weighs the parameters scores 72. Its purpose is to differentiate the impact of individual parameters on microbial health. Every individual parameter score 72 output by the scoring algorithm 70 is weighed using a corresponding weighing function which outputs the final score 72 of the parameter. Physically it means some parameters are more critical and vital than others to maintain a healthy microbial population responsible for the treatment.

After weighing, the indexing algorithm 78 sums the final scores 72 of all the measured parameters into a total score. The total score is then normalized as a ratio to the maximum optimal score. The outcome is the index value reflecting the health of the desirable microbial population.

Health index values 80 are ranged to a list of descriptive textual indicators that include no action in the best case to very specific corrective interventions in the problematic cases.

TABLE 1

|  | VALUE | | SCORE | |
| --- | --- | --- | --- | --- |
|  | Measured | Benchmark | Measured | Maximum |
| Floc morphology | | | | |
| Floc diameter (mµ) | 150–500 (20% flocs < 150) | 150–500 | 3 | 3 |
| Floc shape/structure | round,firm,compact | round,firm,compact | 3 | 3 |
| Filament abundance | few to some | none to some | 3 | 3 |
| Total filament length (cm/mg) | 200 | <700 | 3 | 3 |
| Higher life form | rotifers,swimming,stalked clliates, crawling clliates and testate amoeba | diverse | 3 | 3 |
| Settleability | | | | |
| dSVI (mL/g) | 48 | 50–150 | 3 | 3 |
| SSV5 (mL/L) | 140 | 500–700 | 1 | 3 |
| SSV30 (mL/L) | 120 | 250–350 | 1 | 3 |
| Effluent TSS | 9 | <50 | 3 | 3 |
| Type of settling problem | Rapid settling | Normal | 2 | 3 |
| Microbial activity | | | | |
| SOUR - first cell (mg O2/h/g) | 16 | 10–25 | 3 | 3 |
| SOUR - last cell (mgO2/h/g) | 12 | 1–5 | 1 | 3 |
| Load index - Fed/Unfed OUR | 1.3 | 2–5 | 1 | 3 |
| BOD removal efficiency (%) | 97 | >90 | 3 | 3 |
| Microtox toxicity (EC50, %) | >100 | 100 | 3 | 3 |
| Sludge age - AST (d) | 5 | 5–9 | 3 | 3 |
| Aerobic heterotrophs (cfu/ml) | 6.8E+07 | 10E7–10E8 | 3 | 3 |
| Floc nutrient balance | | | | |
| Soluble phosphorus (mg/L) | 0.84 | 0.3–0.8 | 3 | 3 |
| Soluble ammonia-nitrogen (mg/L) | 2.3 | 1.5–2.5 | 3 | 3 |
| Sludge polysaccharide (%) | 14 | 15–20 | 2 | 3 |
| BOD:N:P | 100:6.3:0.4 | 100:3:0.5 to 100:5:1 | 2 | 3 |
| P/MLVSS (%) | 0.8 | >0.9 | 2 | 3 |
| N/MLVSS (%) | 7.7 | >9 | 2 | 3 |
| MLVSS/MLSS (%) | 75 | >65 | 3 | 3 |
|  |  | Total score | 59 | 72 |

OVERALL INDEX  0.8

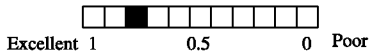

Excellent 1          0.5          0 Poor

COMMENT:  SETTLING TOO FAST
ACTIVITY RELATIVELY MARGINAL
AMMONIA ADDITION IN EXCESS

FIG. 4 is a simple flow chart showing that measured parameters of the effluent are fed to the data base and that the effluent parameters are adjusted where necessary in response to the information from the data base, following the comparison and generation of the holistic health index.

FIG. 5 is a more detailed flow chart illustrating the sequence of operations.

I claim:

1. A knowledge based system for generating a holistic health index for diagnosis and decision support in operational management of biological treatment of waste water in which a microbial population contained within said waste water consumes organic waste in the water, and in which operational conditions of the biological treatment affect the activity and performance of the microbial population comprising:

a) data base means having a store of benchmark values of a plurality of first parameters for biological treatment of waste water with a first microbial population, said plurality of first parameters comprises parameters of said first microbial population and parameters of an environment of said first microbial population for optimum biological performance of the first microbial population, b) input means for acquiring measured values of second parameters in an operating biological treatment of waste water with a second microbial population contained within said waste water for consumption of organic waste and removal of toxicity in the waste water, said second parameters corresponding to at least some of said first parameters, and comprising parameters of said second microbial population and parameters of the waste water environment containing second microbial population, c) comparison means for comparing said measured values of second parameters with corresponding first parameters of said benchmark values and generating a comparison value for each of said parameters, and d) index generating means for generating a holistic health index of said second microbial population from the comparison values, said health index providing an evaluation of the operational management of the biological treatment of the waste water containing said second microbial population.

2. A system according to claim 1, wherein the first microbial population is an optimally performing population.

3. A system according to claim 1 further including:

e) means to capture images of said second microbial population.

4. A system according to claim 3 further including:

f) means for introducing the captured images into said data base; said benchmark values including images of said first microbial population.

5. A system according to claim 3 further including:

g) means for transmission of said images to a remote site for evaluation.

6. A method of generating a holistic health index for diagnosis and decision support in operational management of biological treatment of waste water with a microbial population comprising:

i) establishing a data base with stored benchmark values associated with a plurality of parameters for the biological treatment of waste water, with a first microbial population, ii) measuring operating values of said parameters in a biological treatment of waste water associated with a second microbial population, iii) comparing said operating values with said benchmark values and generating a comparison value for each of the parameters, and iv) generating a holistic health index of said second microbial population from the comparison values, said health index providing an evaluation of the operation of the biological treatment with said second microbial population.

7. A method according to claim 6, wherein the first microbial population is an optimally performing population and the steps ii), iii) and iv) are repeated continually.

8. A method according to claim 6 further including a step of capturing images of said second microbial population.

9. A method according to claim 8, further including feeding the captured images into said data base; said benchmark values including images of said first microbial population.

10. A method according to claim 6, wherein said waste water in step ii) is a pulp and paper mill waste water developed in pulp and paper manufacture.

11. A method for managing biological treatment of waste water with a microbial population comprising:

i) establishing a database with stored benchmark values associated with a plurality of parameters for the biological treatment of waste water, with a first microbial population, ii) measuring operating values of said parameters in a biological treatment of waste water associated with a second microbial population, iii) comparing said operating values with said benchmark values and generating a comparison value for each of the parameters, iv) generating a holistic health index of said second microbial population from the comparison values, said health index providing an evaluation of the operation of the biological treatment with said second microbial population, and v) adjusting said operating values in response to the holistic health index to maintain said biological treatment at an optimum level.

12. A method according to claim 10, wherein said biological treatment in step ii) is carried out in a secondary treatment tank.

13. A method according to claim 11, wherein said waste water in step ii) is a pulp and paper mill waste water developed in pulp and paper manufacture.

* * * * *